(12) United States Patent
Lauf et al.

(10) Patent No.: US 10,932,820 B2
(45) Date of Patent: Mar. 2, 2021

(54) STATIC STRUT AND FIXATION CONSTRUCTS

(71) Applicant: Life Spine, Inc., Huntley, IL (US)

(72) Inventors: Garrett D. Lauf, Hampshire, IL (US); Matthew S. Coyne, Algonquin, IL (US)

(73) Assignee: Life Spine, Inc., Huntley, IL (US)

( * ) Notice: Subject to any disclaimer, the term of this patent is extended or adjusted under 35 U.S.C. 154(b) by 21 days.

(21) Appl. No.: 16/177,405

(22) Filed: Oct. 31, 2018

(65) Prior Publication Data

US 2019/0125407 A1    May 2, 2019

Related U.S. Application Data

(60) Provisional application No. 62/579,402, filed on Oct. 31, 2017.

(51) Int. Cl.
*A61B 17/64* (2006.01)
*A61B 17/62* (2006.01)
*A61B 17/66* (2006.01)

(52) U.S. Cl.
CPC .......... *A61B 17/6425* (2013.01); *A61B 17/62* (2013.01); *A61B 17/66* (2013.01)

(58) Field of Classification Search
CPC .............................................. A61B 17/60–688
See application file for complete search history.

(56) References Cited

U.S. PATENT DOCUMENTS

| | | | | |
|---|---|---|---|---|
| 4,308,863 A | * | 1/1982 | Fischer | A61B 17/62 606/56 |
| 6,030,386 A | * | 2/2000 | Taylor | A61B 17/62 606/54 |
| 2002/0143338 A1 | * | 10/2002 | Orbay | A61B 17/8042 606/287 |
| 2010/0312243 A1 | * | 12/2010 | Ross | A61B 17/645 606/56 |
| 2010/0331840 A1 | * | 12/2010 | Ross | A61B 17/6475 606/54 |
| 2011/0208187 A1 | * | 8/2011 | Wong | A61B 17/6416 606/59 |

(Continued)

FOREIGN PATENT DOCUMENTS

WO    2009/102904 A1    8/2009

*Primary Examiner* — Nicholas J Plionis
(74) *Attorney, Agent, or Firm* — Foley & Lardner LLP

(57) ABSTRACT

A static fixation strut for constructing external orthopedic fixation constructs has a ball joint component, a piston component axially adjustably coupled to the ball joint component, and a swivel component coupled to the piston component opposite the ball joint component, the ball joint component for attachment to a first fixation ring, the swivel component for attachment to a second fixation ring, and the piston component for adjusting the overall length of the static fixation strut. The ball joint component provides a multi-axial adjustable connection to the first fixation ring, the piston component provides adjustability in axial length between the ball joint component and the swivel component via first and second cylinders, and the swivel component provides a rotationally adjustable connection to the second fixation ring. A C-clamp is disposed about the first and second cylinders to fix their axial movement and length.

6 Claims, 6 Drawing Sheets

(56) References Cited

U.S. PATENT DOCUMENTS

| | | | |
|---|---|---|---|
| 2012/0041439 A1* | 2/2012 | Singh | A61B 17/60 606/54 |
| 2013/0123784 A1 | 5/2013 | Ross et al. | |
| 2013/0204248 A1* | 8/2013 | Singh | A61H 3/00 606/56 |
| 2015/0313641 A1 | 11/2015 | Ross et al. | |
| 2017/0020576 A1* | 1/2017 | Siccardi | A61B 17/7037 |
| 2017/0303966 A1* | 10/2017 | Edelhauser | A61B 34/10 |
| 2017/0354439 A1* | 12/2017 | Mannanal | A61B 17/62 |
| 2018/0368887 A1* | 12/2018 | Lauf | A61B 17/62 |

\* cited by examiner

STATIC STRUT AND FIXATION CONSTRUCTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/579,402 filed Oct. 31, 2017 titled "Static External Fixator Strut and Fixation Construct," the entire contents of which is specifically incorporated herein by reference.

FIELD OF THE INVENTION

The present invention relates to components for external orthopedic fixation and, more particularly, to struts for external orthopedic fixation.

BACKGROUND OF THE INVENTION

External fixation, as an alternative to internal fixation, is a surgical approach to stabilize bone and soft tissues at a distance from the injury that uses fixation constructs assembled from various fixation components. External fixation may be done for various bones and/or areas of the body such as, but not limited to, the arm, spine, leg, ankle, and foot. It provides unobstructed access to the relevant skeletal and soft tissue structures for their assessment and intervention(s) needed to restore bony continuity and a functional soft tissue cover.

In this kind of surgical approach, holes are drilled into uninjured areas of bones around the desired orthopedic problem/area and special bolts or wires are screwed into the holes. Outside the body, one or more fixation rings surround the desired orthopedic area, the fixation rings connected to one another by one or more struts in order to make a rigid support. The struts adjust in order to configure the fixation construct into a desired anatomical position. Depending on the purpose and/or other considerations of the fixation construct, various types of struts may used in the fixation construct. One type of fixation strut is known as a static fixation strut.

Without being limiting, it is thus an object of the present invention to provide a static fixation strut for external fixation constructs and the external fixation constructs using the static fixation strut. This and other non-limiting objects are satisfied by the present invention.

SUMMARY OF THE INVENTION

A static fixation strut for external orthopedic fixation constructs is characterized by a ball joint component, a piston component axially adjustably coupled to the ball joint component, and a swivel component axially coupled to the piston component opposite the ball joint component, the ball joint component for attachment to a first fixation construct constituent (e.g. ring), the swivel component for attachment to a second fixation construct constituent (e.g. ring). The ball joint component provides a poly-axial (universal) adjustable connection to the first fixation construct constituent, the piston component provides adjustable axial movement (i.e. length) between the ball joint component and the swivel component, and the swivel component provides a rotationally adjustable connection to the second fixation construct constituent.

The ball joint is characterized by a first bolt having a spherical head forming a portion of the ball (universal) joint and a threaded shaft extending from the spherical head for threaded connection to a fixation construct constituent, a spherical housing for receipt of the spherical head of the first bolt, a second bolt having a head with a semi-spherical cavity forming another portion of the ball joint and a threaded shaft for threaded connection to another fixation construct constituent.

The piston component is characterized by a grommet with an internally threaded bore for threaded connection to the threaded shaft of the second bolt for axial (length) adjustment between the ball joint and the grommet (piston component), a first cylinder (piston component constituent) connected to the grommet and forming a portion of an axially (length) adjustable piston, a second cylinder (piston component constituent) axially movably disposed over the first cylinder and forming another portion of the axially adjustable piston, and a C-clip that allows the first and second cylinders to adjustably translate relative to each other to increase or decrease axial length of the piston component and thus the overall strut. Once this C-Clip is tightened the static fixation strut is then axially locked. The second cylinder also includes tangs on one end for connection to the swivel component forming a portion of a swivel joint between the second cylinder and the swivel component.

The swivel component is characterized by third bolt having a head adapted for reception by the tangs of the second cylinder of the piston component forming another portion of the swivel joint, a swivel pin pivotally connecting the head to the tangs of the second cylinder, a shaft extending from the head and having a non-threaded section proximate the head and a threaded section distal the head, a shoe configured for receipt by the threaded section of the shaft of the third bolt, and cutouts on the non-threaded section for coupling the shoe to the third bolt with a coupling pin.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWING FIGURES

The features of the invention will be better understood by reference to the accompanying drawings which illustrate a form of the present invention, wherein.

DETAILED DESCRIPTION OF THE INVENTION

Figure 1:
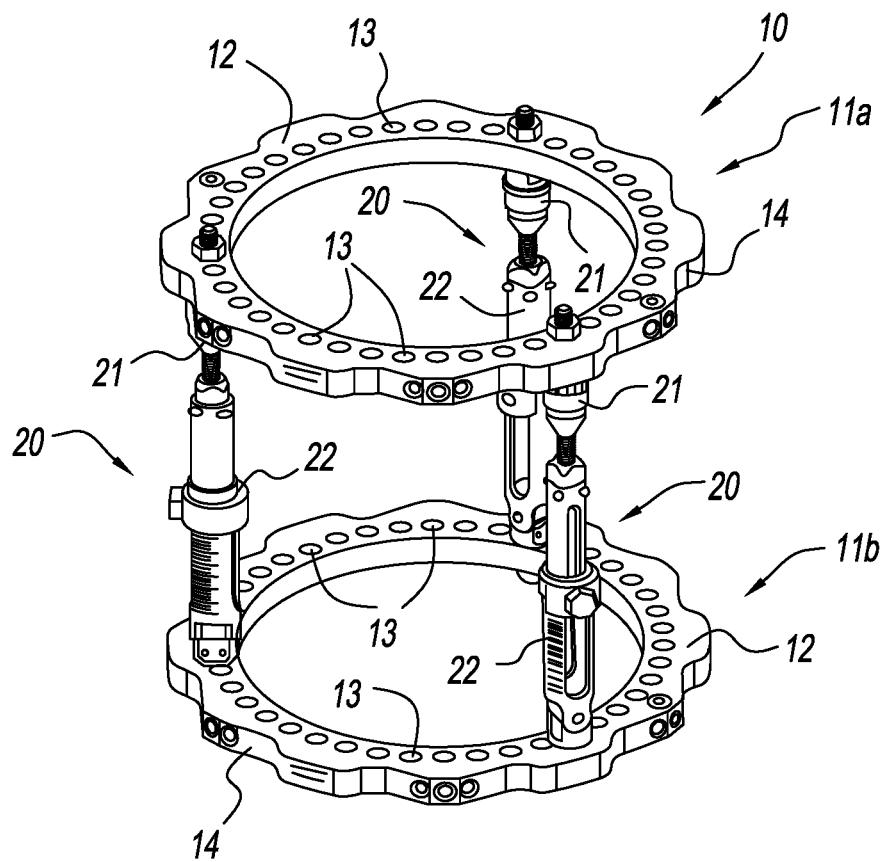
FIG. 1 is an isometric view of an exemplary external fixation construct using static fixation struts fashioned in accordance with the principles of the present invention.
Figure 2:
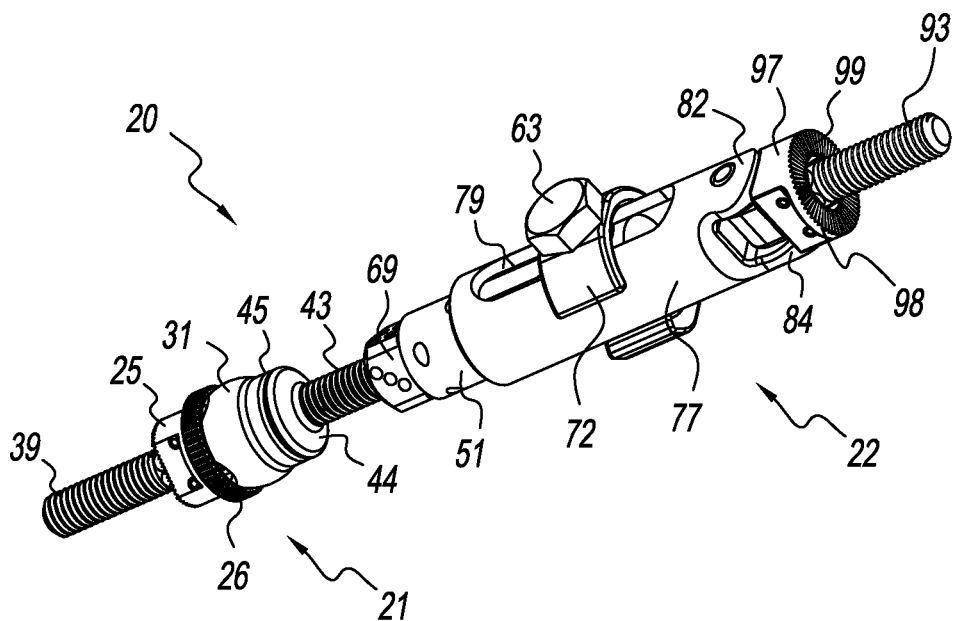
FIG. 2 is an isometric view of the present static fixation strut.
Figure 3:
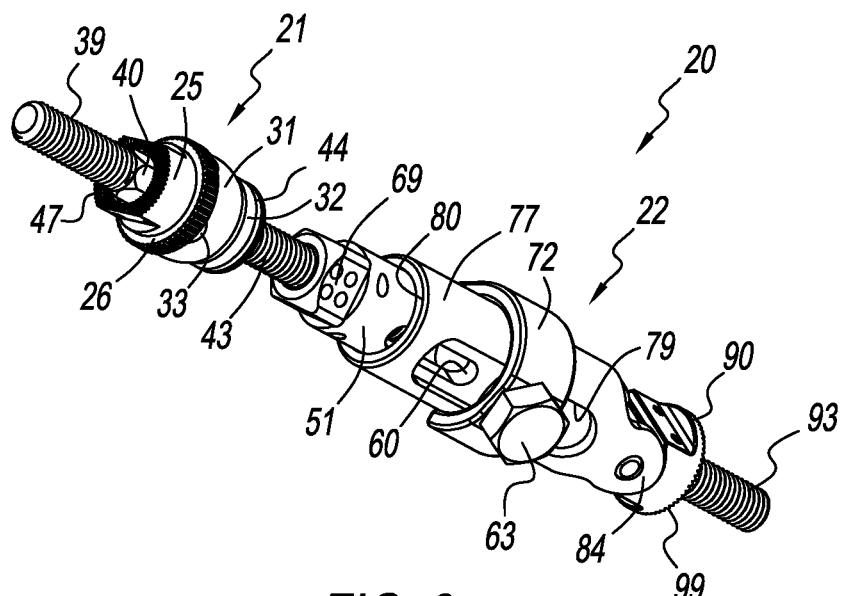
FIG. 3 is another isometric view of the present static fixation strut.
Figure 4:
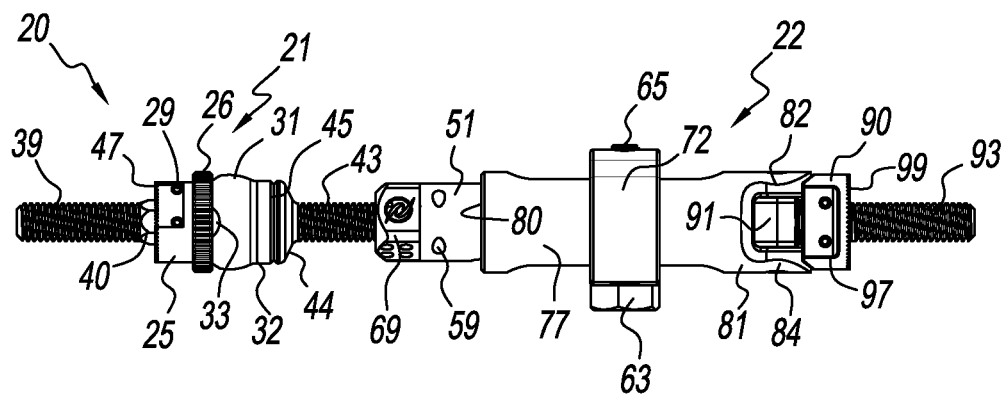
FIG. 4 is a side view of the present static fixation strut.
Figure 5:
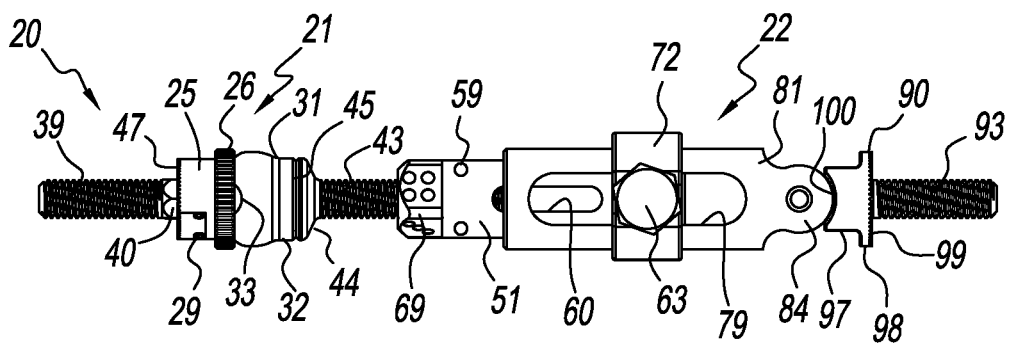
FIG. 5 is another side view of the present static fixation strut.
Figure 6:
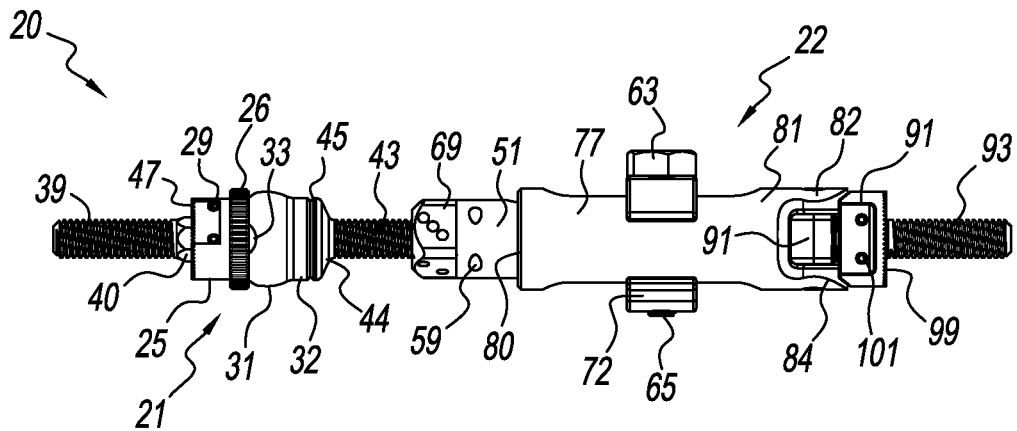
FIG. 6 is a further side view of the present static fixation strut.
Figure 7:
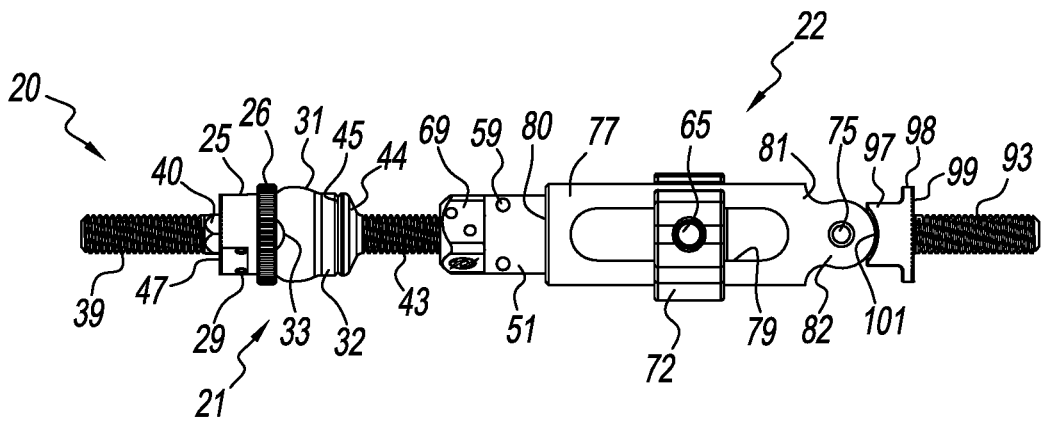
FIG. 7 is a still further side view of the present static fixation strut.
Figure 8:
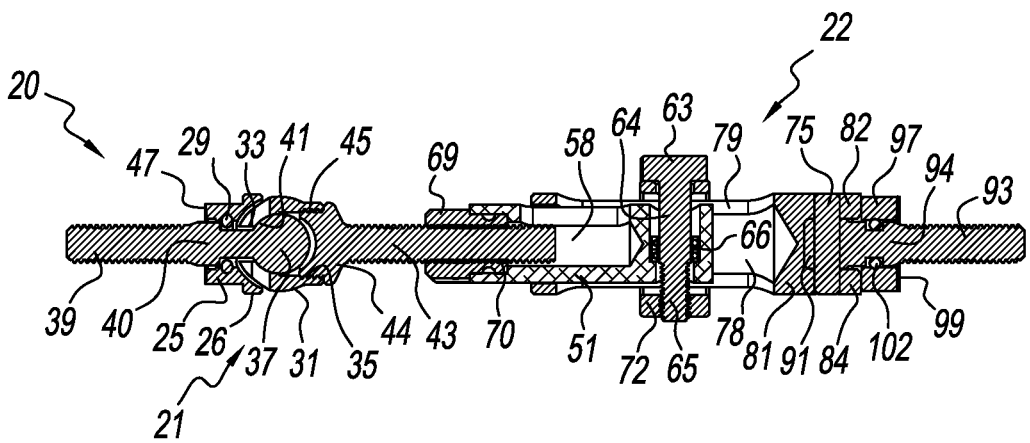
FIG. 8 is a side sectional view of the present static fixation strut.
Figure 9:
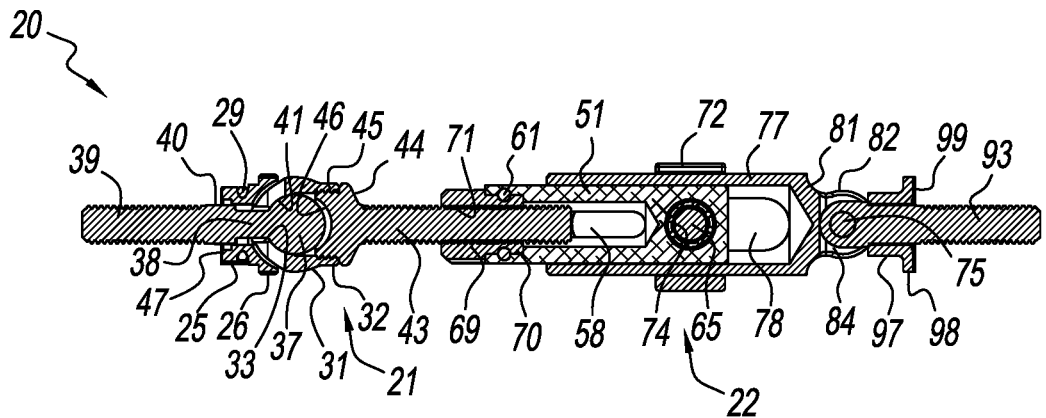
FIG. 9 is another side sectional view of the present static fixation strut.

FIG. 1 shows an exemplary external fixation construct, fixator, or the like 10 that utilizes the present static fixation strut 20. The external fixation construct 10 uses a first fixation ring 11a and a second fixation ring 11b. Each fixation ring 11 has a generally annular body 12 having a plurality of holes 13 situated about the annular body 12 and a configured perimeter 14. While three (3) static fixation struts 20 are used in the exemplary external fixation construct 10 shown in FIG. 1, more or less static fixation struts 20 may be used. Of course, other types of external fixation constructs may be constructed as well as other configurations.

Referring to FIGS. 2-17, there is shown various views of a static strut/strut 20 for use in external orthopedic fixators/fixation constructs fashioned in accordance with the present principles. The static fixation strut 20 shown in FIGS. 1-17 is designed to allow for a quick connection between two fixation rings (see FIG. 1) or the like (i.e. components) of a fixation construct. The present static fixation strut 20 is fashioned from a bio-compatible material such as is known in the art.

The external fixation strut 20 has a ball joint component 21, a piston component 22, and a swivel component 88. The piston component 22 provides axial length adjustment of the fixation strut. The ball joint component 21 is connected to one axial end of the piston component 22 to be axially (length) adjustable with respect to the piston component 22 and is configured to provide multi or poly axial (universal) movement/motion between the ball joint component 21 and a fixation construct constituent (e.g. ring 11a). The swivel component 88 is connected at the axial end of the piston component 22 opposite the ball joint component 21 and is configured to provide pivotal movement/motion between the swivel component 88 and the piston component 22 to provide pivotal movement/motion between another fixation construct constituent (e.g. ring 11b) and the strut 20.

Figure 10:
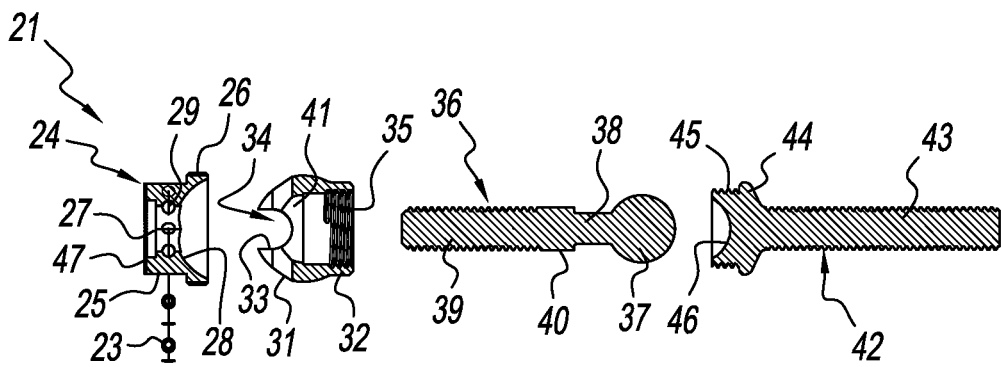
FIG. 10 is a side sectional view of the ball joint component of the present static fixation strut.
Figure 11:
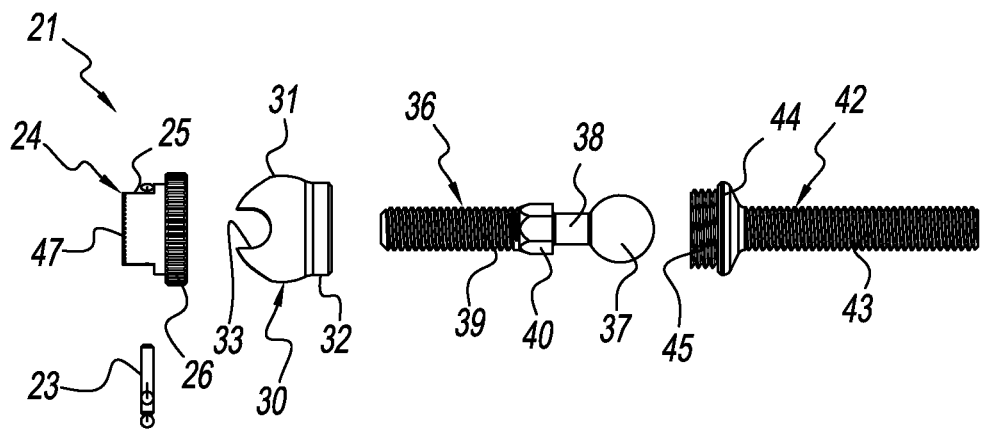
FIG. 11 is a side view of the ball joint component of the present static fixation strut.
Figure 12:
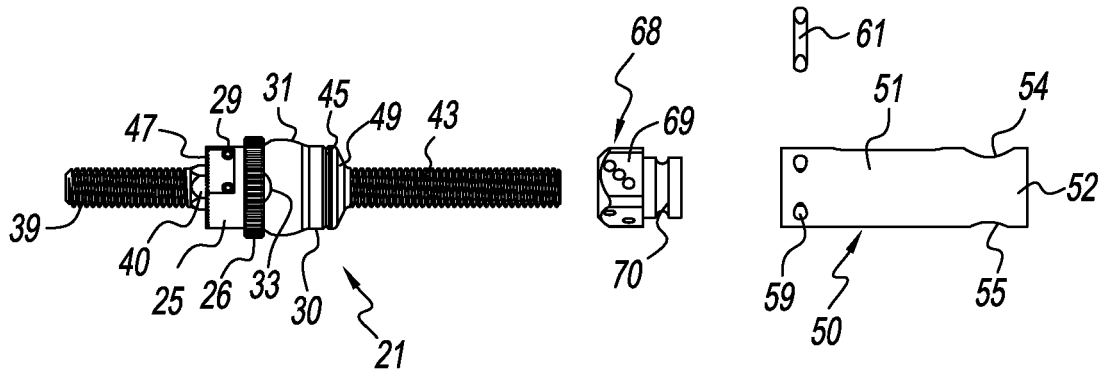
FIG. 12 is a side view of the ball joint component relative to a first piston constituent of the piston component of the present static fixation strut.
Figure 13:
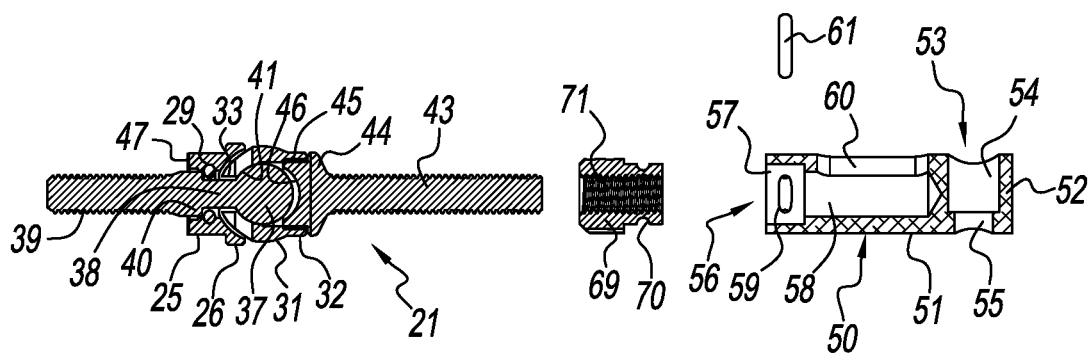
FIG. 13 is a side sectional view of the ball joint component relative to the first piston constituent of the piston component of the present static fixation strut.
Figure 14:
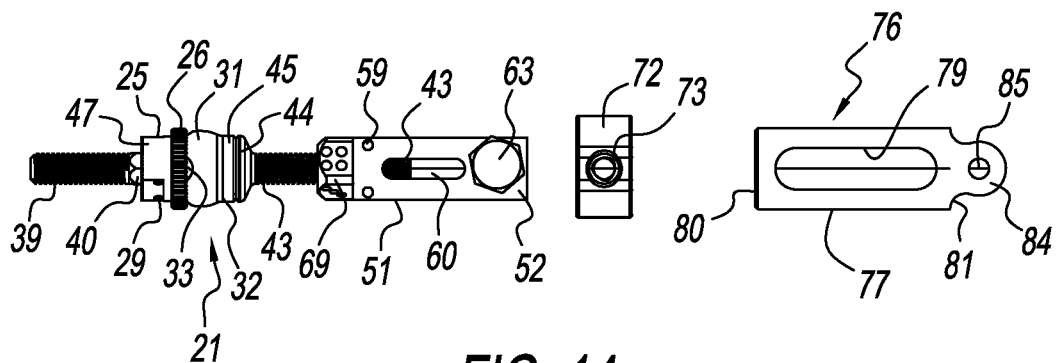
FIG. 14 is a side view of the ball joint component and the first piston constituent of the piston component relative to the second piston constituent of the piston component and C-clamp.

As best seen in FIGS. 10-11, the ball joint component 21 has a ball joint formed by a cap 24, a head 30, and head 44 of bolt 42 and, specifically semi-spherical cavity 46 of the head 44. The cap 24 is defined by a generally cylindrical portion 25 with a second, larger generally cylindrical portion 26 having a knurled perimeter axially above the cylindrical portion 25, the inside of the cylindrical portion 25 having a semi-spherical cavity 28 that defines/provides at least a partial seat for a ball head 37 of a first bolt 36 of the ball joint component 21. A bore 27 extends through the cap 24 and is co-axial with the semi-spherical cavity 28. The end 47 of the cylindrical portion 25 is serrated for gripping a fixation component. A channel 29 is provided about the bore 27 that is configured to receive a staple/pin 23. The channel 29 and pin 23 axially retains the first bolt 36.

The head 30 is defined by generally spherical hood 31 having a neck 32 at one side and a notch 33 at another side. A bore 34 extends through the spherical hood 31 from the notch 33 to the neck 32. The neck 32 has internal threads 35. The inside 41 of the hood 31 defines at least a partial seat for the ball head 37 of the first bolt.

The ball joint component 21 further includes the first bolt 36 having a threaded shaft 39 with a neck 38 terminating in the ball head 37. A nut 40 is provided between the threaded shaft 39 and the neck 38. The first bolt 36 provides the threaded shaft 39 for threaded connection to a fixation component/constituent, and the ball head 37 as part of the ball joint. The ball joint moreover includes the second bolt 42 having a threaded shaft 43, a head 44 on the threaded shaft 43 and external threads 45 on the head 44. The external threads 45 mate with the internal threads 35 of the hood 31. The head 44 also includes the semi-spherical cavity 46 providing at least a part of the ball joint and adapted to extend about the head 37 of the first bolt 36.

The piston component 22 has a collet 68 with a base 69 and a configured end 70. The collet 68 includes a threaded bore 71 that is configured to threadedly join with the threaded shaft 43 of the ball joint component 21 to provide axial, adjustable connection to the ball joint component 21. The piston component 22 has a first piston cylinder 50 and a second piston cylinder 76. The first cylinder 50 is characterized by a cylindrical body 51 having a longitudinal bore 56 extending from one axial end of the cylinder body 51 into its interior. The bore 56 has a larger diameter entry 57 and a small diameter channel 58 that is sized to receive the threaded shaft 43 of the ball joint component 21. The larger diameter entry 57 allows receipt of the configured end 70 of the collet 68 to join the collet 68 to the inner cylinder 50. The inner cylinder 50 includes openings 59 to receive a pin 61. The collet 68 is attached to the cylinder 50 by the pin 61 in the openings 59 and extending about the configured end 70 (see e.g. FIG. 8).

An opening 60 is provided in the sidewall of the cylinder body 51 that provides a window into the interior 58. The end 52 of the cylindrical body 51 opposite the bore opening 56 has a bore 53 that extends through the end 52 transverse to the longitudinal bore 56. The transverse bore 53 has a larger diameter opening 54 on one side of the cylinder sidewall and a smaller diameter opening 55 one an opposite cylinder sidewall. The transverse bore 53 is sized to receive a bolt 62 (see e.g. FIG. 15) of the axial adjustment mechanism of the piston component 22. A bushing 66 is preferably, but not necessarily, disposed in the transverse bore 53 (see e.g. FIGS. 8 and 15). The bolt 62 is characterized by a hexagonal (or other configuration) head 63 with an unthreaded shaft portion 64 extending from the underside of the head 63 and a threaded shaft portion 65 at the axial end of the unthreaded shaft portion 64. The bolt 62 cooperates with a C-clamp 72 having an opening 73 on one side that is sized to receive the unthreaded shaft portion 64 of the bolt 62, and a threaded opening 74 on an opposite side that threadedly receives the threaded shaft portion 65 in order to tighten and loosen the C-clamp 72. The C-clamp 72 is situated about the first and second cylinders 50, 76.

The second cylinder 76 is characterized by a cylindrical body 77 having a longitudinal bore 78 extending from one axial end 80 of the cylinder body 77 into its interior. The longitudinal bore 78 is sized so the second or outer cylinder or sleeve 76 fits over and around the first or inner cylinder 50 such that the longitudinal axis of the outer cylinder 76 is co-axial with the longitudinal axis of the inner cylinder 50. The first and second cylinders 50, 76 are axially movable with respect to one another, providing axial length adjustment for the piston component 22. A bore 79 extends transverse to the longitudinal bore 78 and has a very large opening such that the bore 79 may be considered a window to allow viewing of the first cylinder 50 relative to the second cylinder 76 and of the threaded shaft 43 of the second bolt 44 of the ball joint component 21. This provides a gauge of the length of the strut 20.

Figure 15:
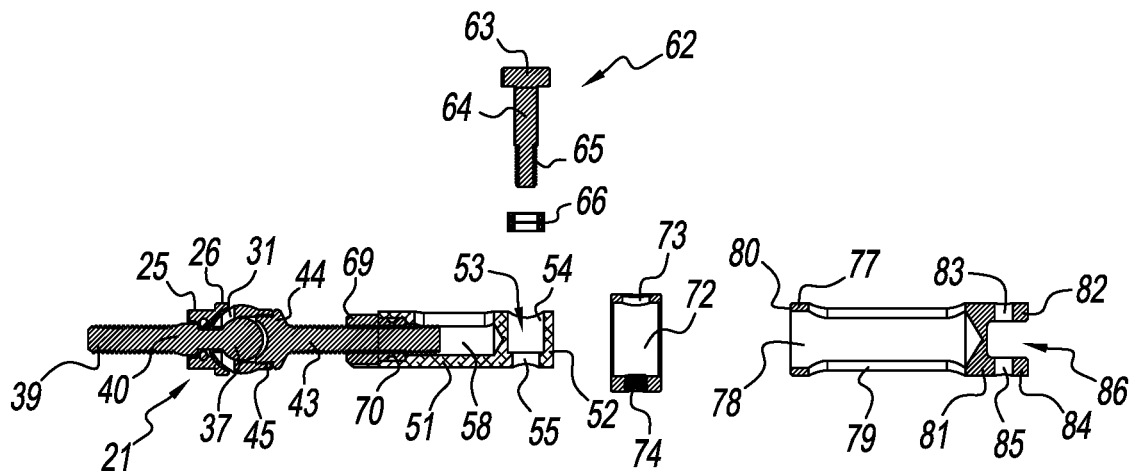
FIG. 15 is a side sectional view of the present static fixation strut.
Figure 16:
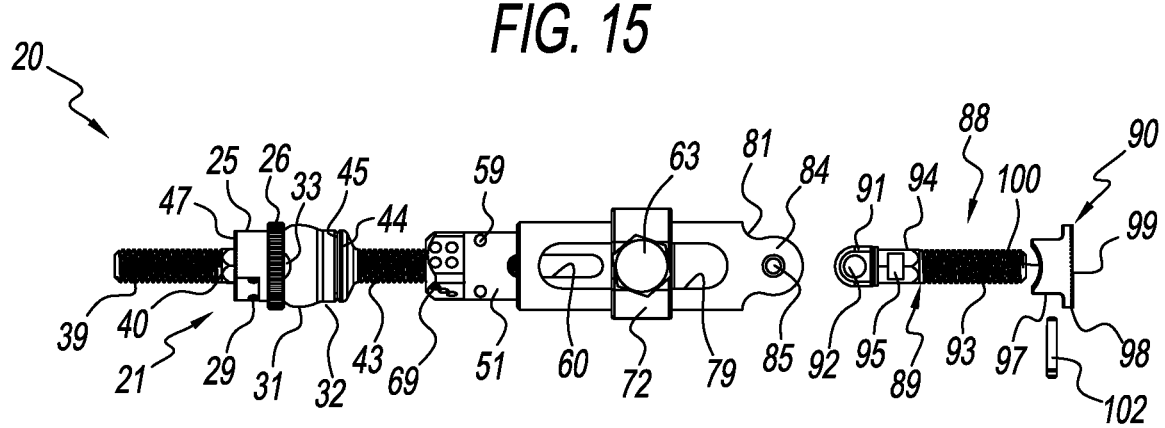
FIG. 16 is side view of the present static fixation strut.

The end 81 has a swivel joint portion defined by a first tang 82 extending axially outwardly from the end 81 and a second tang 84 extending axially outwardly from the end 81 and a pocket 86 formed between the first and second tangs 82, 84 (see e.g. FIG. 15). The first tang 82 has a central bore 83 while the second tang 84 has a central bore 85 for receipt of a pivot pin 75.

Figure 17:
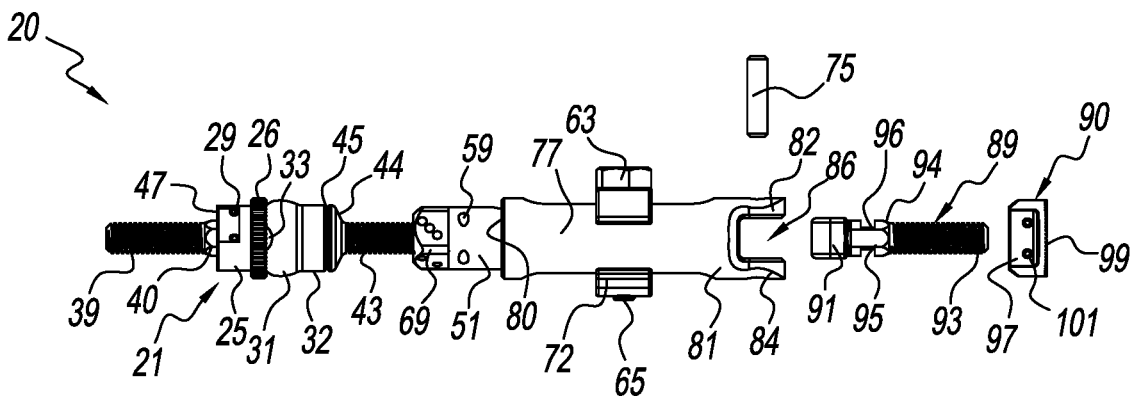
FIG. 17 is another side view of the present static fixation strut.

The swivel joint component 88 includes a body 89 and shoe 90. The body 89 is fashioned as a bolt having a threaded shaft 93 connected to a swivel joint portion 91 formed as a head via a nut portion 94. As seen in FIG. 17, the swivel joint portion (head) 91 of the swivel component 88 is received in the pocket 86 of the outer cylinder 76 to provide a swivel joint that allows pivoting motion between the outer cylinder 76 and the body 89 and thus a fixation construct constituent connected thereto. The nut portion 94 includes a first notch 95 and a second notch 96 (see e.g. FIG. 17) that allows the body 89 to be connected to the shoe 90 (see e.g. FIG. 8). The shoe 90 has a cylindrical portion 97 having a semi-spherical end 100, and a serrated end 99 opposite the semi-spherical end 100. The shoe 90 is received on the shaft 93.

It should be appreciated that the ball joint component 21 is axially adjustable with respect to the piston component 22, that the piston component 22 is axially adjustable with respect to itself, and that the swivel component 88 is pivotally adjustable with respect to the piston component 22 and to a fixation construct constituent. The ball joint component 21 adjusts universally with respect to the piston component 22 and to a fixation construct constituent.

It should furthermore be appreciated that dimensions of the components, structures, and/or features of the present static fixation strut may be altered as desired within the scope of the present disclosure.

What is claimed is:

1. A fixation strut for an external fixation construct, the fixation strut comprising:
    a ball joint component having a first bolt with a spherical head forming a first portion of a ball joint and a first threaded shaft extending from the spherical head for threaded connection to a first fixation construct constituent, a spherical housing for receipt of the spherical head of the first bolt, a second bolt having a second head with a semi-spherical cavity forming a second portion of the ball joint, and a second threaded shaft extending from the second head of the second bolt;
    an axially adjustable piston having a grommet with an internally threaded bore for threaded connection to the second threaded shaft of the second bolt providing length adjustment between the ball joint and a grommet end, a first cylinder having a first end that fixedly receives the grommet end via a connecting pin and forming a portion of the axially adjustable piston, the first cylinder having a first cylinder bore at a second end and extending radially through the second end of the first cylinder, and a second cylinder axially movably disposed over the first cylinder and forming another portion of the axially adjustable piston, the second cylinder having a first slot in and through a first side of the second cylinder that extends axially along the first side, and a second slot in and through a second side of the second cylinder that extends axially along the second side, the second slot positioned opposite the first slot;
    a clamp that allows the first and second cylinders to adjustably translate relative to each other to increase or decrease axial length of the axially adjustable piston and thus the overall length of the fixation strut and when tightened axially locks position of the first cylinder relative to the second cylinder, the clamp including a band extending around a substantial portion of the second cylinder and over the first and second slots of the second cylinder, the band having a first hole in a wall of the band positioned over the first slot of the second cylinder, and a second hole in the wall of the band positioned over the second slot of the second cylinder, the second hole having internal threading, the clamp further having a bolt extending through the first and second holes of the band wall and through the first and second slots of the second cylinder and the first cylinder bore, the bolt having a threaded shaft that is received by the threading of the second hole; and
    a swivel component having a shoe pivotally coupled to an end of the second cylinder that is opposite the first cylinder, the swivel component having a third bolt with a third head that is received in the shoe, the third bolt having a shaft extending from the third head having a non-threaded section proximate the head and a threaded section distal the head for reception to a second fixation construct constituent, the third head having an axial bore on the non-threaded section for coupling the shoe to the third bolt with a swivel pin.

2. The fixation strut of claim 1, further comprising:
    a swivel pin pivotally connecting the head of the third bolt and the shoe to the second cylinder.

3. The fixation strut of claim 2, wherein:
    the second cylinder includes a first tang and a second tang on one axial end for receiving the head of the third bolt via the swivel pin.

4. The fixation strut of claim 3, wherein:
    the first tang has a first tang bore extending therethrough; and
    the second tang has a second tang bore extending therethrough;
    the first and second tang bores sized for receipt of the swivel pin.

5. The fixation strut of claim 1, wherein the spherical housing comprises:
    a first housing component having an internal spherical seat for receipt of the spherical head of the first bolt; and
    a second housing component having a second internal spherical seat for receipt of the spherical head of the first bolt.

6. The fixation strut of claim 5, wherein:
the first housing component includes internal threads; and
the second bolt has external threads on the head;
the first housing component threadedly receiving the second bolt.

* * * * *